United States Patent [19]

Ciammaichella et al.

[11] Patent Number: 4,667,157

[45] Date of Patent: May 19, 1987

[54] LINEAR HALL EFFECT OXYGEN SENSOR WITH AUXILIARY COIL MAGNETIC FIELD BALANCING

[75] Inventors: Richard C. Ciammaichella, Chardon; Barry J. Youmans, Rittman, both of Ohio

[73] Assignee: The Babcock & Wilcox Company, New Orleans, La.

[21] Appl. No.: 596,482

[22] Filed: Apr. 3, 1984

[51] Int. Cl.$^4$ .................. G01N 27/74; G01R 33/12
[52] U.S. Cl. .................. 324/204; 73/27 A; 324/202; 324/225
[58] Field of Search .............. 324/204, 202, 225, 445, 324/464; 73/27 A, 861.11

[56] References Cited

U.S. PATENT DOCUMENTS

| | | | |
|---|---|---|---|
| 2,930,970 | 3/1960 | Vollmer | 324/204 |
| 3,049,665 | 8/1962 | Hummel | 324/204 |
| 3,076,929 | 2/1963 | Gillerman | 324/204 |
| 4,464,296 | 8/1984 | Albarda et al. | 324/204 X |

FOREIGN PATENT DOCUMENTS

| | | | |
|---|---|---|---|
| 83289 | 1/1982 | Japan | . |
| 984560 | 2/1965 | United Kingdom | 324/204 |
| 773486 | 10/1980 | U.S.S.R. | 324/204 |
| 0974240 | 11/1982 | U.S.S.R. | 324/225 |

Primary Examiner—Gerard R. Strecker
Attorney, Agent, or Firm—Vytas R. Matas; Robert J. Edwards

[57] ABSTRACT

An oxygen sensor utilizes the paramagnetic property of oxygen to determing the relative concentration of oxygen in a test gas. The test gas is supplied to the core of an electromagnet or the gap of a permanent magnet. A known magnetic flux density for the electromagnet or permanent magnet are utilized in conjunction with a Hall effect sensor to determine a change in flux which is primarily due to the oxygen component of the test gas.

5 Claims, 4 Drawing Figures

LINEAR HALL EFFECT OXYGEN SENSOR WITH AUXILIARY COIL MAGNETIC FIELD BALANCING

FIELD AND BACKGROUND OF THE INVENTION

The present invention relates in general to gas sensors and in particular to a new and useful oxygen sensor which utilizes the paramagnetic properties of oxygen and a Hall effect sensor to determine the amount of oxygen in a gas.

It is often important to measure the concentration of oxygen in various gases. The use of an oxygen sensor for sensing the oxygen content in flue gases of combustion processes can be utilized to determine the efficiency of combustion.

Presently known detectors of $O_2$ include the following:

Wet chemical cells which suffer short life spans and require frequent recalibration;

Zirconium oxide sensors which are fragile, poisoned by common flue gas constituents, require high operating temperatures and are difficult to manufacture;

Paramagnetic analyzers which use the oxygen's paramagnetic properties to create a situation in which the $O_2$ concentration can be inferred from thermal conductivity measurements, or pressure measurements, where the inference is inaccurate due to effects of bulk gas composition, temperature and instrument attitude; and Magnetodynamic analyzers which derive the susceptibility, by measuring force due to movement of a sample gas through a magnetic field, but are limited due to the low forces exerted and either linearity or vibration and shock resistance must be compromised.

SUMMARY OF THE INVENTION

The inventive method of $O_2$ measurement differs from those described above in that it measures the susceptibility of the gas directly using a linear Hall effect sensor. Since the measurement is not dependent upon interference from the thermal conductivity or temperature effects, carrier gas composition presents less error. The only inferferant which is known to be of potential significance is Nitric Oxide (NO), which has a relative susceptibilty 43% that of oxygen at room temperature (see the Table). However, the relative volume of NO to $O_2$ in a typical flue gas mixture is less than 1/20, which reduces the calibration error to the range typically specified for zirconia based sensors. Careful control of the analyzer at elevated temperatures can further reduce this error. For typical application of offset zero would eliminate error due to normal (usually constant) NO concentrations. Since the sensor is a solid-state, non-contact device; life expectancy, linearity, and shock resistance are superior to present online oxygen sensors.

The proposed invention uses the Hall effect to directly measure the paramagnetic influence of oxygen.

Paramagnetism is the property of certain substances wherein a magnetic field applied to the substances will increase by the alignment of electron orbits of the substances. The magnetic permeability of paramagnetic materials is slightly greater than that of empty space. Paramagnetic materials are contrasted from diamagnetic materials in that diamagnetic materials slightly reduce a magnetic field applied to them and have a magnetic permeability which is slightly less than that of empty space.

The relatively high susceptibility (and thus paramagnetic property) of oxygen over that of most other gases and specifically most of the gases that would be found in flue gas, makes the paramagnetic property of oxygen useful as a measuring tool.

| Relative magnetic susceptibilities on the scale nitrogen = 0, oxygen = 100 | | | |
|---|---|---|---|
| Acetylene, $C_2H_2$ | −0.24 | Hydrogen $H_2$ | +0.24 |
| Allene, $C_3H_4$ | −0.44 | Hydrogen bromide, HBr | −0.61 |
| Ammonia, $NH_3$ | −0.26 | Hydrogen chloride, HCl | −0.30 |
| Argon, Ar | −0.22 | Hydrogen fluoride, HF | +0.10 |
| Bromine, Br2 | −1.3 | Hydrogen iodide, HI | −1.1 |
| 1,2-Butadiene, $C_4H_6$ | −0.65 | Hydrogen sulphide, $H_4S$ | −0.39 |
| 1,3-Butadiene, $C_4H_6$ | −0.49 | Krypton, Kr | −0.51 |
| n-Butane, $C_4H_{10}$ | −1.3 | Methane, $CH_4$ | −0.2 |
| Isobutane, $C_4H_{10}$ | −1.3 | Neon, Ne | +0.13 |
| 1-Butene, $C_4H_5$ | −0.85 | Nitric oxide, NO | +43 |
| cis-2-Butene, $C_4H_5$ | −0.89 | Nitrogen, $N_2$ | 0.0 |
| Isobutene, $C_4H_5$ | −0.85 | Nitrogen dioxide, $NO_2$ | +28 |
| trans-2-Butene, $C_4H_5$ | −0.92 | Nitrous oxide, $N_2O$ | −0.2 |
| Carbon dioxide, $CO_2$ | −0.27 | n-Octshe, $C_5H_{12}$ | −2.5 |
| Carbon monoxide CO | +0.01 | Oxygen, $O_2$ | 100 |
| Chlorine, $Cl_2$ | −0.77 | n-Pentane, $C_5H_{12}$ | −1.45 |
| Ethane, $C_2H_4$ | −0.46 | Isopentane, $C_5H_{12}$ | −1.49 |
| Ethylene, $C_2H_4$ | −0.26 | Neopentane $C_5H_{12}$ | −1.49 |
| Helium, He | +0.30 | Propane, $C_3H_5$ | −0.86 |
| n-Heptane, $C_7H_{16}$ | −2.1 | Propylene, $C_3H_4$ | −0.545 |
| n-Hexane, $C_6H_{11}$ | −1.7 | Water, $H_2O$ | −0.02 |
| Cyclohexane, $C_6H_{12}$ | −1.557 | Xenon, Xe | −0.95 |

The Hall effect is a phenomona wherein, when a conductor of ribbon shape is exposed to a magnetic field whose direction is transverse to a current in the ribbon, an electrostatic field appears whose direction is perpendicular both to the magnetic field and the direction the flow of charge due to the current. This effect is utilized in a Hall effect sensor which in turn can be used to measure a change in magnetic field due to the presence of oxygen in a gas to be tested, which gas is supplied to the core of an electromagnet or gap of a permanent magnet, whose nominal magnetic flux is known.

Hall effect output ($P_H$) is proportional to magnetic flux density (B) and the flux generated by an electromagnet can be expressed in terms of permeability ($\mu$), number of turns in the coil (n), current through the coil (I) and the radius of the coil (r) by the equation:

$$P_H = \frac{\mu n I}{2 r} \quad (1)$$

The coil radius and number of turns are obviously constants and the current can be controlled as desired. Hence the only variable which affects the flux (and proportionately the Hall output) is the permeability $\mu$ which is dependent upon the material in the space of the field.

By passing the sample containing oxygen through the core of an electromagnetic (or the gap of a permanent magnet) the gas composition can be computed from the changing flux knowing its permeability or susceptibility by the equation:

$$X = \frac{\mu - 1}{\mu_o} \quad (2)$$

Where

X = susceptibility
μ = permeability of the gas
$\mu_o$ = permeability of the volume The volume susceptibility of a mixture is proportional to the concentration of its constituents and inversely to temperature. Oxygen has a volume susceptibility of $141.3 \times 10^{-9}$ as opposed to $60.3 \times 10^{-9}$ for nitric oxide, $-9.39 \times 10^{-9}$ for nitrogen, $-0.165 \times 10^{-9}$ for hydrogen, $-0.78$ for $10^{-9}$ for carbon dioxide, $-1.67 \times 10^{-9}$ for methane and $-1.88 \times 10^{-9}$ for propane. Hence an electromagnet core will produce a higher flux density if filled with oxygen than with other flue gases. Nitric oxide is the only major interferent known but will not cause a significant error in normal flue gas concentrations.

Note that the change in field from 100% $O_2$ to 100% $N_2$ will be very small in proportion to the absolute value of the applied field:

$$Ba\mu \quad (3)$$

for $O_2 = (141.3 \times 10^{-9} + 1)$ for $N_2 = (-0.39 \times 10^{-9} + 1)$ $$\frac{\mu O2}{\mu N2} = 1.0000014$$

However, if a very strong magnetic field is applied, the absolute change in B is very large:

$$B \cdot \mu H \text{ so that if H (magnetic field) is very large, e.g.}$$
$$H = 10^6, \Delta B = 1.4 = 0.000014\% \ B. \quad (4)$$

Then, to measure accurately with the Hall effect sensor, span must equal ΔB and be offset to read zero at B nominal. This can be accomplished by adding a second magnet whose field opposes the first (μB) and is not affected by $O_2$ concentration. This second magnet could also be used to cancel magnetic variation due to changing temperature power supply effect etc. by utilizing an electromagnet similar to the first. Pulsing both also allows error cancelling of the magnetic permeance as done in magnetic flowmeters.

Accordingly, an object of the present invention is to provide a method of detecting oxygen concentration in a gas, comprising, applying a known current to an electromagnet to produce a magnetic field in a core of the electromagnet having a known nominal magnetic flux density;

supplying the gas to the core of the electromagnet; and measuring a change in the magnetic flux density of the electromagnet while the known current is applied thereto which change is substantially proportional to oxygen concentration in the gas.

A further object of the present invention is to provide such a method wherein the change in magnetic flux density is measured utilizing a Hall effect sensor to measure a Hall effect output which results from the paramagnetic property of the oxygen concentration in the gas.

A still further object of the invention is to provide such a method wherein the gas is flue gas from a combustion process.

Another object of the invention is to provide an oxygen detector for measuring oxygen concentration in a gas, comprising an electromagnet having a core, means for supplying the gas to the core, and magnetic flux measuring means associated with the electromagnet for measuring flux density of the magnetic field produced by the electromagnet when it is activated, and to measure changes in the flux due to the passage of gas having the oxygen concentration to be measured, the change in flux density being proportional to the amount of oxygen in the gas.

A still further object of the invention is to provide an oxygen detector which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREPERRED EMBODIMENT

Figure 1:
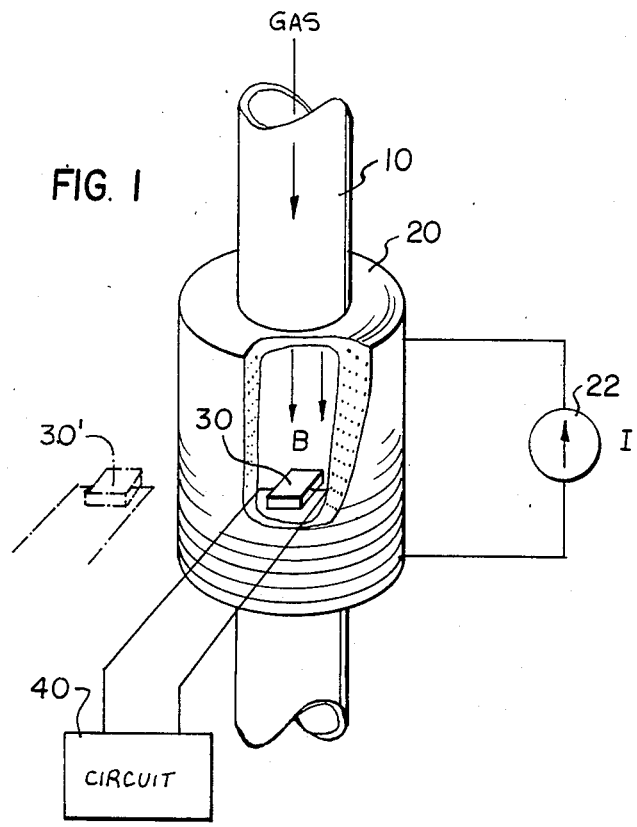
FIG. 1 is a perspective view with portions cut away for clarity of an oxygen detector in accordance with the invention.

Referring to the drawings in particular, the invention embodied in FIG. 1 comprises an oxygen detector for detecting oxygen concentrations in a gas supplied through a tube 10 to the core of an electromagnet 20. Electromagnet 20 comprises a coil having a large number of turns and supplied with a current by current supply means 22. The tube 10 is made of material having known permeability to the magnetic flux density B of a field generated by electromagnet 20 and indicated by the arrows. In the coil of electromagnet 20, a Hall effect sensor 30 is provided for measuring the magnetic flux density B. This flux density changes as the concentration of oxygen in the gas in tube 10 changes and thus can be utilized, using a circuit 40, to provide a measurement of oxygen concentration.

In FIG. 1, a position 30' for the sensor may be used for ease of manufacture. Also, an additional sensor may be provided at 30' to provide the second electromagnet that is used in some forms of the invention. The position 30 for the sensor is, however, the best location for maximum flux density.

Figure 2:
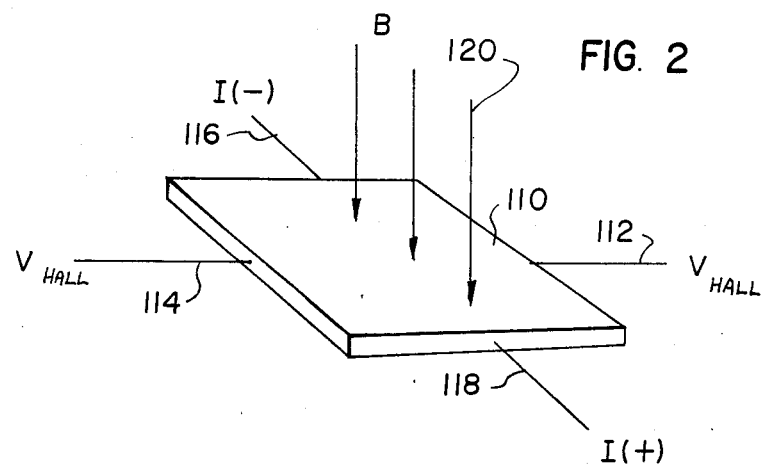
FIG. 2 is a perspective view of a Hall effect sensor used in conjunction with the apparatus of FIG. 1.

Referring to FIG. 2, the body 110 of the sensor is a flat rectangular strip of semiconductor material such as silicon. A current I is passed through the strip in a direction from the lead 118 to the lead 116. The magnetic field B, designated 120, is the physical variable to be sensed and passes through the sensor at a direction perpendicular to its flat surface. The field interacts with the flowing current to produce a voltage at right angles to both I and B appearing between terminals 112 and 114. This voltage is proportional to the product of I and B.

Figure 3:
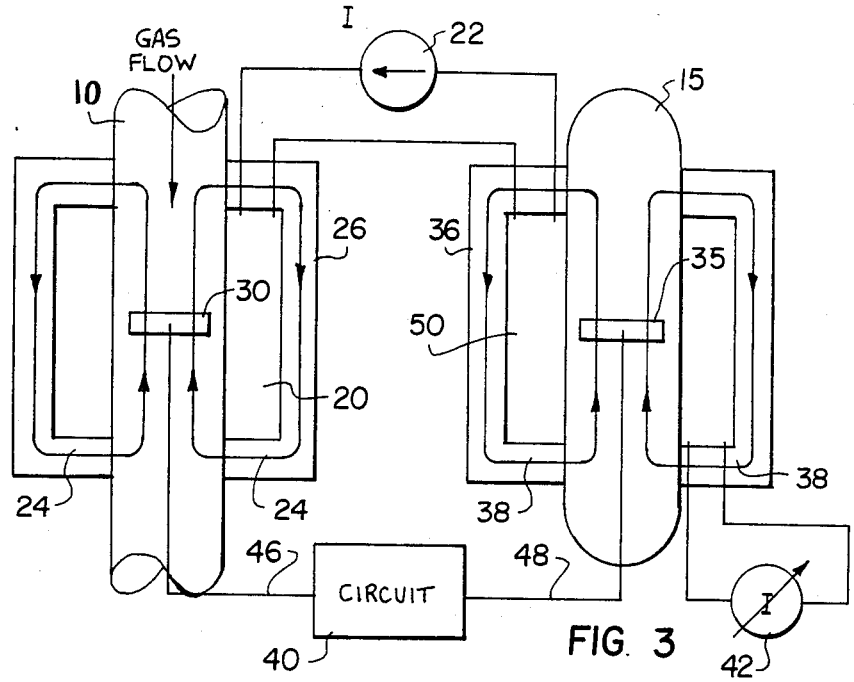
FIG. 3 shows the use of two electromagnets in the invention.

FIG. 3 shows an embodiment of the invention which utilizes two electromagnets 20 and 50. The same numerals are used in FIG. 3 as in FIG. 2, to designate the same or similar parts.

While the core of electromagnet 20 is provided with tube 10 for the measurement of oxygen concentration in a gas carried by the tube, the core of electromagnet 50 is provided with a closed ended tube 15 containing a known gas sample. Any other material having known magnetic permeability may be provided in the core of electromagnet 50. Electromagnets 20 and 50 are chosen to be as identical as possible so that all factors unassociated with the paramagnetism of oxygen are removed from the measurement procedure.

Electromagnets 20 and 50 are supplied by the same current source 22, with the same current.

Hall sensors 30 and 35 are positioned in the fields of electromagnets 20 and 50 which are of identical design as far as practical. An auxiliary coil is included in electromagnet 50 to either buck or aid the field of the main coil. This is used to balance the electromagnet sensor pairs in the absence of $O_2$. Variable current 42 is used for effecting this adjustment.

Field shunts 24 and 38 are used to contain the external fields from electromagnets 20 and 50 respectively. This confines the external paths to known conditions. The gas being measured flows through tube 10. The reference unit contains a sealed tube 15 containing a known gas which is not $O_2$.

Circuit 40 is connected to both sensors 30 and 35 to measure differences in the magnetic flux density of the two cores. When all of the factors are held constant, this measurement gives a signal representation of the $O_2$ concentration in the measuring coil.

Figure 4:
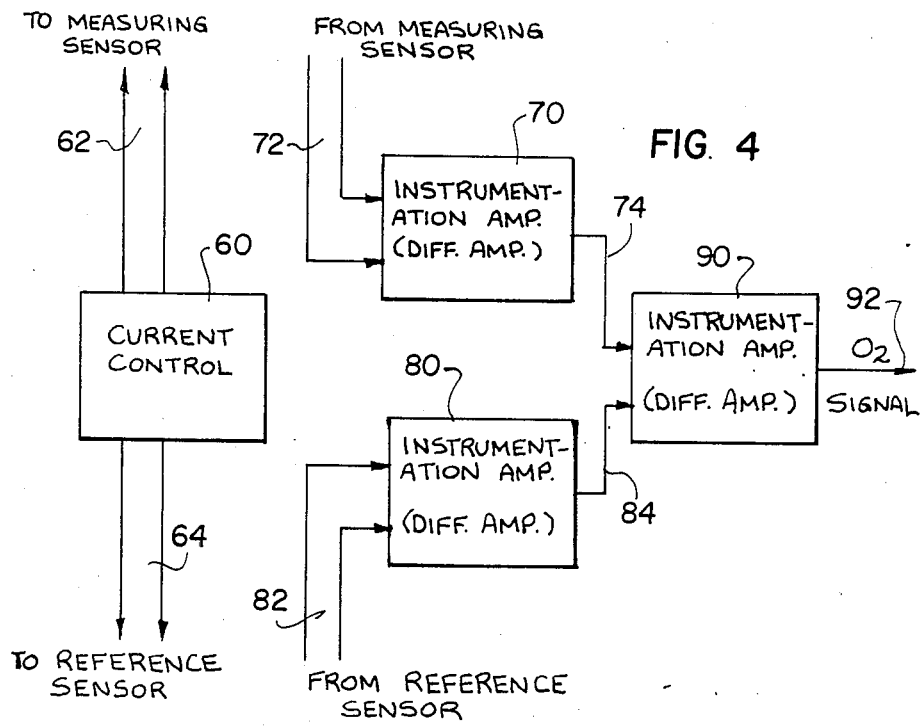
FIG. 4 is a block diagram of a circuit in accordance with the invention.

The circuit 40 is connected to each sensor by four wires, two each for current and two each for induced voltage measurements. FIG. 4 shows a block diagram for this circuit.

Referring to FIG. 4, the sensors are driven by currents generated by the control circuit 60. The currents are maintained identical in amplitude and direction to each other by circuit 60. Lines 62 deliver current to the measuring sensor 30 in FIG. 3, lines 64 deliver current to the reference sensor 35 in FIG 3.

Lines 72 connect the induced Hall effect voltage to the difference or instrumentation amplifier 70. This amplifier provides a a voltage on line 74 proportional to the true difference of voltage between lines 72. Similarly, line 84 gets a signal via amplifier 80 proportional to the voltage difference between lines 82 received from the Hall voltage induced in the reference sensors.

Since the $O_2$ signal is proportional to the difference of voltage between lines 74 and 84, a similar true difference circuit or instrumentation amplifier to that of 70 and 80 is used for 90. Amplifier 90 extracts the $O_2$ related signal from 74 and 84 and presents it on 90.

The instrumentation amplifiers 70, 80 and 90 may employ amplifiers similar to Analog Devices AD 522 or Burr Brown 3626. Improved accuracy is obtained by using three matched and tracking amplifiers, on a single silicon chip or on a hybrid circuit substrate, along with the current sources.

The current used in the Hall effect sensors may be DC and the amplifiers similarly bandwidth limited and ultrastable in DC operation. An alternate mode is to employ a sinewave of current for the sensors and amplifiers tuned to this frequency. The AC or sinewave implementation will permit a much higher sensitivity of operation.

While a specific embodiment of the invention has been shown and described in detail to illustrate the application of the principles of the invention, it will be understood that the invention may be embodied otherwise without departing from such principles.

What is claimed is:

1. An oxygen detector for measuring oxygen concentration in a gas, comprising:
   a first electromagnet having a first core;
   a second electromagnet substantially identical to said first electromagnet, said second electromagnet having a second core;
   a material of known magnetic permeability disposed in said second core;
   means for passing current of a known value through said first electromagnet for generating a magnetic field having a known nominal magnetic flux density in said first core, said means for supplying a current connected to said second electromagnet to generate in said second core of said second electromagnet substantially the same nominal magnetic flux density as said first electromagnet;
   means for conducting the gas through said first core;
   a first Hall Effect sensor located within said first core at a position corresponding to substantially the maximum flux density of said first core;
   a second Hall effect sensor located within said second core at a position corresponding to substantially the maximum flux density of said second core;
   an auxiliary coil connected to said second electromagnet for receiving a variable current to balance the magnetic fields in said first and second cores in the absence of oxygen in the gas; and
   means connected to said first and second Hall Effect sensors for measuring any changes in the magnetic flux density between said first and second cores which changes are proportional to oxygen concentration in the gas.

2. An oxygen detector according to claim 1, wherein said means connected to said first and second Hall Effect sensors measures the change in the magnetic flux density of said first core with respect to the nominal magnetic flux density of said second core.

3. An oxygen detector according to claim 1, wherein said Hall Effect sensors provide signals corresponding to the induced Hall Effect voltage in said Hall Effect sensors.

4. An oxygen detector according to claim 3, including a first differential amplifier connected to said first Hall Effect sensor for receiving a first signal corresponding to the induced Hall Effect voltage in said first Hall Effect sensor, a second differential amplifier connected to said second Hall Effect sensor for receiving a second signal corresponding to the induced Hall Effect voltage in said second Hall Effect sensor, and a third differential amplifier connected to said first and second differential amplifiers for receiving said first and second signals and providing an output signal corresponding to the difference between said first and second signals, said output signal being proportional to the oxygen concentration in the gas.

5. An oxygen detector according to claim 1, wherein said means for passing current through said first and second electromagnet is pulsed, thereby minimizing the magnetic permeance of said first and second electromagnet.

* * * * *